United States Patent [19]

Cerda-Olmedo et al.

[11] Patent Number: 5,643,719
[45] Date of Patent: Jul. 1, 1997

[54] INTERSEXUAL HETEROZYGOUS PHYCOMYCES

[75] Inventors: Enrique Cerda-Olmedo; Bina Jamnadas Mehta, both of Sevilla, Spain; Petrus Wilhelmus Maria Van Dijck, Utrecht; Bertus Pieter Koekman, Schipluiden, both of Netherlands

[73] Assignee: Gist-brocades, N.V., Ma Delft, Netherlands

[21] Appl. No.: 157,159

[22] PCT Filed: Apr. 5, 1993

[86] PCT No.: PCT/EP93/00850

§ 371 Date: Feb. 2, 1994

§ 102(e) Date: Feb. 2, 1994

[87] PCT Pub. No.: WO93/20198

PCT Pub. Date: Oct. 14, 1993

[30] Foreign Application Priority Data

Apr. 3, 1992 [EP] European Pat. Off. .............. 92200958
May 8, 1992 [EP] European Pat. Off. .............. 92201313

[51] Int. Cl.⁶ .............. C12Q 1/68; C12P 23/00; C12N 15/64; C12N 1/15

[52] U.S. Cl. .............. 435/6; 435/67; 435/172.3; 435/254.8; 435/254.11

[58] Field of Search .............. 435/254.11, 254.8, 435/67, 172.3, 6

[56] References Cited

U.S. PATENT DOCUMENTS 2,865,814  12/1958  Hesseltine et al. .............. 435/67
2,890,989  6/1959   Anderson .............. 435/67
4,318,987  3/1982   Araujo et al. .............. 435/172.3

OTHER PUBLICATIONS

T. Ootaki, in *Phycomyces*, E. Cerda-Olmedo and E.D. Lipson (eds.), CHS Laboratory Press, 1987, pp. 345–349.
T. Suarez et al., in *Phycomyces*, E. Cerda-Olmedo and E.D. Lipson (eds.), CHS Laboratory Press, 1987, pp. 351–353.

*Primary Examiner*—James S. Ketter
*Attorney, Agent, or Firm*—Morrison & Foerster LLP

[57] ABSTRACT

The present invention discloses intersexual heterozygous Phycomyces strains. These strains show an improved β-carotene productivity and an increased stability when compared with both the wild type and heterokaryotic Phycomyces strains. The present invention also discloses a method for obtaining Phycomyces transformants without using selection markers. Furthermore, a process is provided for manufacturing β-carotene comprising the use of intersexual heterozygous Phycomyces strains in a submerged culture.

7 Claims, No Drawings

INTERSEXUAL HETEROZYGOUS PHYCOMYCES

FIELD OF THE INVENTION

The present invention relates to the microbial production of carotenoids. Specifically, the invention relates to the production of β-carotene by intersexual heterozygous Phycomyces strains. The invention also relates to purified β-carotene obtained after fermentation with these strains.

BACKGROUND OF THE INVENTION

In the late fifties and early sixties Mucorales strains, in particular *Blakeslea trispora, Choanephora cucurbitarum* and *Phycomyces blakesleeanus* have been studied in order to develop a fermentation process for the production of carotenoids. Wildtype strains of these fungi accumulate carotenoids, in particular β-carotene. However, the amounts that can be obtained with pure cultures are insignificant for commercial production.

β-carotene is a lipid-soluble yellow chemical with provitamin A and reportedly with anticancer activities. Various applications in the food, feed, cosmetics, chemicals and pharmaceutical industries are reported.

Several processes that increase the β-carotene production are based on the co-cultivation of strains of opposite mating type, (+) or (−). The interaction between mycelia of opposite mating types leads the formation of trisporic acids and to enhanced β-carotene accumulation. Co-Is cultivation of *Blakeslea trispora* strains of opposite mating type in a batch-type fermentation process was developed by Hesseltine and Anderson (U.S. Pat. No. 2,865,814 and U.S. Pat. No. 2,890,989). Up to pilot-plant scale the process looked a promising way to produce β-carotene. β-Ionone was added to stimulate β-carotene production of the two strains within the fermentor. In later years this process was optimized by several industrial companies. Numerous other additives have been used to stimulate the β-carotene accumulation. However, these developments no longer were pursued as it became clear that these processes could not compete on a cost-price level with chemical processes to manufacture β-carotene on an industrial scale.

Nowadays only in the former USSR a plant is in use to produce β-carotene from *Blakeslea trispora*. Agricultural waste-products are used as raw materials for the fermentation and the β-carotene obtained is used as a feed-additive.

Meanwhile academic research focussed on the biochemistry and regulation of β-carotene biosynthesis using the filamentous fungus *Phycomyces blakesleeanus* as a convenient model system. The synthesis of β-carotene in Phycomyces is subject to strict metabolic regulation. Mutations of the regulatory genes may overcome this strict regulation. Classical mutation experiments resulted in the development of strains with a strongly increased β-carotene productivity even in the absence of stimulatory factors. Wildtype Phycomyces strains in the dark contain about 50 μg β-carotene per gram dry weight of biomass. Regulatory single mutants have been found to contain up to 6 mg β-carotene/g dry weight. Double mutants have been isolated which contain over 10 mg β-carotene per gram dry weight.

*Phycomyces blakesleeanus* is a filamentous fungus with hyphae containing no transverse cell walls (septa), thus the whole mycelium may be viewed as a single collective cell or coenocyte containing millions of nuclei. Unlike other fungi the hyphae never fuse together. Therefore, fusion can only be achieved by using artificial methods such as protoplast fusion or microsurgery or by transplantation of structures of the sexual cycle (T. Ootaki in Phycomyces, E. Cerdá-Olmedo and ED Lipson eds. (1987), CSH Laboratory Press, 345–349; T. Suarez et al., Ibid 351–353). Reproduction of the fungus can take place either through a sexual cycle involving zygospores and germspores or by vegetative reproduction (Phycomyces, E. Cerdá-Olmedo and E. D. Lipson eds., (1987) CSH Laboratory Press, 2).

The germspores that are the meiotic products of the mating process of two strains of opposite mating type and the resulting mycelia are usually homokaryotic, i.e. all their nuclei are genetically identical, however a few heterokaryotic germspores are formed spontaneously even in normal crosses. As a consequence some of the germspores give rise to intersexual heterokaryons which contain a mixture of (+) and (−) nuclei.

Such heterokaryons are morphologically different from the normal mycelia. The mycelia show a bright color due to the increased accumulation of β-carotene and characteristic structures, so-called pseudophores, are formed.

The maintenance and propagation of intersexual heterokaryons is difficult since the nuclei show a clear tendency to segregate leading to sectors of mycelia having nuclei of one mating type only. The construction of intersexual heterokaryotic strains, wherein both the nuclei contain a recessive lethal mutation, to minimize the segregation of nuclei, has been the strategy by which F. J. Murillo Araujo et al. (U.S. Pat. No. 4,318,987) have succeeded to construct superproducing strains. These strains which can be described as stabilized intersexual heterokaryons of deregulated mutants were found to produce β-carotene up to 25 mg/g dry weight.

However, even with these recessive lethal mutations, controlling the nuclear ratio to a certain extent, the intersexual heterokaryotic strains are not optimally suited for β-carotene production. These intersexual heterokaryotic strains grow much worse than wild type strains and moreover they seldom or never sporulate.

SUMMARY OF THE INVENTION

The present invention discloses intersexual heterozygous Phycomyces strains.

The present invention also discloses that intersexual heterozygous Phycomyces strains show an increased stability and that they grow better than the previously available intersexual heterokaryons, they also show an increased β-carotene productivity compared with the other available stable strains.

The present invention further provides a method for obtaining intersexual heterozygotes of heterothallic Mucorales, particularly Phycomyces, more particularly *Phycomyces blakesleeanus*.

The present invention also provides a transformation procedure for Phycomyces that does not use a selection marker.

The invention further provides a method for producing β-carotene comprising the use of intersexual heterozygous *Phycomyces blakesleeanus* strains. This method optionally comprises the use of submerged culturing of the Phycomyces strains of the present invention.

The invention also provides β-carotene obtained by purifying the β-carotene after growth of the heterozygous strains.

DETAILED DESCRIPTION OF THE INVENTION

The present invention discloses intersexual heterozygous Mucorales strains, particularly Phycomyces strains, more particularly *Phycomyces blakesleeanus* strains.

In the context of this invention the denotation intersexual heterozygote is used for the total spectrum of Phycomyces strains ranging from strains with a completely diploidic genome to strains which are diploids with respect to the mating type genes only. Due to the fact that all strains at least contain the mating type genes of both parents they may be termed intersexual heterozygotes.

The intersexual heterozygous Phycomyces strains of the present invention show better growth performance and sporulation than balanced-lethal intersexual heterokaryons. These strains also have a higher β-carotene production than wild type strains and than strains which carry the same deregulatory mutations but which are not intersexual.

To date diploid Phycomyces strains have not been described in the Phycomyces literature. Attempts to obtain diploids through nuclear fusion in heterokaryotes have so far failed. The large nuclei found in a certain strain of Phycomyces were conjectured to be diploid by Robinow (C. F. Robinow, Can. J. Microbiol. 3 (1957), 791–798). E. Cerdá-Olmedo and E. D. Lipson, Phycomyces (1987) (Cold Spring Harbor Laboratory Press), provides an extensive and almost exhaustive overview of current knowledge concerning Phycomyces.

The present invention describes the construction of intersexual heterozygous Phycomyces strains and the production of β-carotene with these strains.

Intersexual heterozygotes can be made in several ways. Two of them will be outlined here. One method is fusion of complete nuclei obtained from strains of opposite mating type to form fully diploid nuclei. Non-disjunction of chromosome I during meiosis or random loss of other chromosomes during mitotic multiplication of the diploid will yield partial diploids, all of which are within the scope of the present invention. Another method is the introduction of a copy of one mating type locus into the nucleus of a strain having the other mating type.

The following methods can be used to obtain intersexual heterozygous strains;

a) crossing of selected strains, giving rise to a low frequency of diploids or, b) transformation of a sporangium of one mating type with the genes from the other mating type. In this case preferably the mating type gene is transformed.

The intersexual heterozygous *Phycomyces blakesleeanus* strains of the present invention have been obtained in both ways.

Transformation procedures for Phycomyces have been described (T. Suarez, Ph.D. Thesis (1985), University of Salamanca, Spain; J. L. Revuelta and M. Jayaram, Proc. Nat. Acad. Sci. U.S.A. 83 (1986), 7344–7347; T. Suarez and A. P. Eslava, Mol. Gen. Genet. 212 (1988), 120–123; J. Arnau et al., Mol. Gen. Genet. 212 (1988), 375–377). Protoplast transformation is used to introduce plasmids containing desired DNA into the recipient strain. The low transformation frequencies obtained by these authors make it unlikely that transformants containing an extra copy of the mating type will show up.

T. Ootaki et al. (Japan J. Genet. 66 (1991), 189–196), describe a method in which the transformation efficiency is considerably increased. Microinjection is used increasing the transformation frequencies to 10%. Nevertheless G418 is used as a selection marker.

The present invention describes a new transformation procedure which operates without the use of a selection marker, using microinjection. The method results in intersexual heterozygous Phycomyces. The method comprises the following steps;

isolating the DNA of a Phycomyces strain having either a (+) or a (−) mating type, cloning this DNA in a suitable vector which does not require a selection marker, introducing the obtained vector via microinjection into a Phycomyces strain of the opposite mating type, screening for intersexual heterozygous strains.

Another possibility of obtaining transformants is the use of uncloned DNA of either one of the mating types. This has the advantage that no foreign DNA is introduced.

For obtaining strains which are heterozygous for the mating type locus, strains having either the (+) or the (−) mating type can be used as acceptor strains. Low β-carotene producing strains can be used as starting strains, alternatively a recipient strain already producing large amounts of β-carotene can be used. Examples of suitable acceptor (+) strains are a wild type strain, e.g. NRRL1554, a carF mutant e.g. S563, or, preferably a mutant carrying both carS and carF mutations e.g. S566. As donor DNA, DNA of a strain of the opposite mating type (−) can be used such as wild type NRRL1555; carF S561 or S562; cars carF S568 or S569.

It may be difficult to select over-producing transformants by visual inspection especially when high producing strains are used as recipient. In that case specific inhibitors of β-carotene biosynthesis such as diphenylamine and the like may be used to suppress the level of color production to allow for selection of overproducing transformants. It is also possible to facilitate the detection of the desired transformants by selecting for cotransformation of the mating type-linked marker colA in a colA$^-$ background. Transformants having acquired the colA$^+$ phenotype will appear as vigorous outgrowth among the colA strains, which have a restricted colony morphology.

Screening for intersexual heterozygous strains can be performed by visual inspection or on the basis of intersexual morphology. Intersexual heterozygous strains can further be characterized by the absence of sexual reaction to tester (+) and (−) strains. Pseudophores form another characterising feature of intersexual heterozygous strains.

Intersexual heterozygous Phycomyces strains obtained contain more than 10 mg/g dry weight of β-carotene after growth of 6 days on plates. Preferably the amount of β-carotene is more than 20 mg/g dry weight, more preferably the amount is more than 25 mg/g dry weight. Growth conditions are plates in the dark, containing minimal solid medium at 22° C.

Further increase in productivity is expected to be obtained by the addition of activators of β-carotene synthesis for example vitamin A, β-ionone or similar compounds known in the art.

EXPERIMENTAL

The minimal glucose-asparagine agar medium which was used for cultivation and β-carotene production of the intersexual heterozygous Phycomyces strains was prepared as follows.

Glucose-Asparagine Agar Medium

Solution A: 2.0 g L-asparagine, 5.0 g $KH_2PO_4$, 20 ml concentrate, 480 ml distilled water.
Solution B: 20 g glucose, 20 g agar, 500 ml distilled water (solid medium).
Autoclave separately and mix.

Concentrate (50x)

To 800 ml distilled water add in the following order each chemical and dissolve well before adding the next one: 25 g MgSO$_4$·7H$_2$O, 100 mg thiamine ·HCl, 5 ml trace element stock, 10 ml calcium stock. Make up the volume to one litre with distilled water, add 2–3 ml chloroform and store at room temperature.

Trace Element Stock

To 100 ml distilled water add in the following order each chemical and dissolve well before adding the next one: 2 g citric acid, 1.5 g Fe(NO$_3$)$_3$·9H$_2$O, 1 g ZnSO$_4$·7H$_2$O, 0.3 g MnSO$_4$·H$_2$O, 0.05 g CuSO$_4$·5H$_2$O, 0.05 g Na$_2$MoO4·2H$_2$O. Add 1–2 ml chloroform and store at room temperature.

Calcium Stock 28 g CaCl$_2$·2H$_2$O, 172 ml distilled water. Add 1–2 ml chloroform and store at room temperature.

Cultivation

Plastic Petri dishes (diameter 8.5 cm), were filled with 25 ml of the above growth and production medium. Inoculation was done with either a piece of vegetative mycelium mat of about 1–25 mm$^2$ or with about 10,000 heat-activated spores.

Spores are heat-activated by raising the temperature of a suspension of spores in distilled water to 48° C. for 10 minutes. After inoculation the plates were incubated in the dark at 22° C. for 5 to 8 days.

Harvest of Mycelium

The mycelium is harvested to extract the β-carotene from it as follows:

The agar-mycelium cake in a plate is taken out upside down onto aluminum foil, the agar is scraped off with the plate lid or a spatula, and the mycelium is pressed gently with filter paper. This is done under normal room light, but the mycelia are kept as much as possible wrapped in aluminum foil, and the extraction is carried out in a small room under subdued light.

β-Carotene Extraction

Mycelia are frozen at −20° C. for 1–2 hours and lyophilized for 16–20 hours. The dry weight is then measured and the mycelium is homogenized with sea sand in a clean mortar with pestle till it becomes a fine powder. The β-carotene is recovered by repeated extraction with petroleum ether (40°–60° C.) until the powder becomes colourless. The extracts are collected in a glass tube kept in an ice bucket and centrifuged at low speed. The clear β-carotene extract is evaporated in a Büchi RE-111 rotavapor at 45° C. and redissolved in 10 ml n-hexane. Dilutions are made if necessary and the absorption spectrum from 250 to 550 nm is recorded. β-carotene content is calculated from the peak extinction coefficient assuming E(1 cm, 1%) =2500 (at a wavelength of 450 nm).

Strains

The following strains have been deposited at the Centraal Bureau voor de Schimmelcultures in Baarn (The Netherlands): *Phycomyces blakesleeanus* S563, S571–S573, S596–S600 on 28 April 1992 under the following accession numbers:

S563, CBS 225.92; S571, CBS 226.92; S572, CBS 227.92; S573, CBS 228.92; S596, CBS 229.92; S597, CBS 230,92; S598, CBS 231.92; S599, CBS 232.92; S600, CBS 233,92.

EXAMPLES

Example 1

Construction of an Intersexual Heterozygous Phycomyces Strain

The *Phycomyces blakesleeanus* deep-yellow beta-carotene superproducer strain S563, carrying the carF mutation and the (+) mating type was crossed with the white (−) strain C2, carrying the carA mutation, following methods known in the art (E. Cerdá-Olmedo and E. D. Lipson Eds., Phycomyces, 361 ff. Cold Spring Harbor Laboratory 1987). Among the progeny of the cross, uniformly deep orange colonies could be isolated lacking a mating type, whose mycelia formed pseudophores, indicative of constitutive sexual interaction. The deep-orange clones were allowed to sporulate and plated on glucose-asparagine agar to check their nuclear stability. These strains are intersexual heterozygotes (S571–S573 and S596–S598).

These intersexual heterozygotes grow normal and appear stable in that they show no segregation in color patches. They produce fewer spores than the normal wild type, a normal feature of all situations involving sexual stimulation. They are far better in growth and sporulation than the superproducing intersexual heterokaryons (F. J. Murillo Araujo et al., Appl. Environ. Microbiol. 36 (1978), 639–642; F. J. Murillo Araujo et al. (1982) U.S. Pat. No. 4,318,987).

A good indication of sexual interaction is the production of trisporic acids, the sexual hormones of the Mucorales. Concentrations of 1–1.4 µg trisporic acids per ml were found in the culture media of three intersexual heterozygotes grown for 8 days in minimal medium with asparagine and monosodium glutamate (0.2 and 2.0 g/l respectively) as nitrogen sources (a medium for sexual interaction (R. P. Sutter, Proc. Natl. Acad. Sci. USA 72. (1975), 127–130). These values correspond to 200–300 µg trisporic acids per g dry weight of mycelium in the cultures. Trisporic acids were chemically extracted and assayed by spectrophotometry (R. P. Sutter, Science 168 (1970), 1590–1592).

Well-growing colonies producing spores that form uniformly deep-orange mycelia were selected for production purposes.

Table 1 shows the β-carotene production of the novel intersexual heterozygotes in comparison with various controls.

TABLE 1

β-carotene production levels of selected Phycomyces strains

| Strain | Nature of the strains | β-carotene * mg/g dry weight |
|---|---|---|
| C2 | car A (−) | 0–<0.001 |
| S563 | car F (+) | 5.60 |
| C2 * S563 | heterokaryon car A * car F | 0.10–0.65 |
| S571 | intersexual heterozygote | 15.8–18.8 |
| S572 | intersexual heterozygote | 11.2 |
| S573 | intersexual heterozygote | 15.6 |

* The cultures were grown for 8 days at 22° C. on glucose-asparagine minimal agar.

Example 2

Construction of an Intersexual Heterozygous Phycomyces Strain

In an alternative approach, both mating types were united in a single nucleus by transforming a mating type gene into a recipient strain having the opposite mating type. To this end, 20 young sporangia of the acceptor strain were injected with 300–400 nanograms of DNA from a lambda gene bank of the donor strain following the procedure as described by Ootaki et el. (Japanese J. of Genetics 66, (1991), 189–195).

As acceptor strains, a β-carotene producing strain having the (+) mating type was used. Here we used the β-carotene producer NRRL1554 as acceptor strain. As donor DNA, DNA isolated from a lambda gene bank containing the DNA of strain NRRL1555, having the opposite mating type was used. To construct the lambda bank NRRL1555 DNA was partially digested with Sau3A and DNA fragments ranging from 12–20 kb were cloned in the BamH1 site of phage lambda 2761 (Avalos, J., L. M. Corrochano and S. Brenner FEBS Lett. 286(1991), 176–180) following methods known in the art.

Since the transformation frequency was of the order of 10%, colonies carrying both mating type loci could be screened directly by their deviant morphology and increased β-carotene content without the need for a selective marker.

Many of the resulting colonies, up to 1%, showed a darker color compared to the background strains. A number of such colonies were purified and were shown to contain up to ten times more β-carotene compared to their parents. These mutants are stable and sporulate normally.

Table 2 shows β-carotene production levels of some selected Phycomyces strains.

TABLE 2

β-carotene production levels of selected Phycomyces strains

| Strain | Nature of the strains | β-carotene * mg/g dry weight |
|---|---|---|
| NRRL1554 | (+) wild type | 0.040 |
| NRRL1555 | (−) wild type | 0.046 |
| S599 | NRRL1554 acceptor NRRL1555 donor | 0.40 |
| S600 | NRRL1554 acceptor NRRL1555 donor | 0.10 |

*The cultures were grown for 8 days at 22° C. on glucose-asparagine minimal agar.

Example 3

Growth of Selected Phycomyces Strains Under Submerged Conditions

Strains S571 and S572 were grown in shake flask cultures as follows. The fermentation medium was prepared as described in the experimental part but omitting the agar from solution B. Erlenmeyer shake flasks of 500 ml were filled with 25 or 100 ml of medium, sterilized according to procedures known in the art and sub-sequently inoculated either with heat-activated spores to a concentration of $0.5 \times 10^5$ spores per ml of medium or with a piece of mycelium mat of 10 –25 mm² obtained from a full-grown agar plate.

Growth and production of β-carotene occurred at 22° C. in the dark.

Cultures of 100 ml were cultivated for 3 days in a rotary shaker (250 rpm)(A), sometimes this incubation was followed by a period of no agitation of 4 days (B).

Cultures of 25 ml were incubated for 12–16 days without any agitation (C).

The results which have been obtained, are shown in Table 3.

TABLE 3

β-carotene production of selected Phycomyces strains in submerged culture

| Strain | β-carotene production mg/g dry weight | Conditions |
|---|---|---|
| S571 | 1.0 | A, spores |
| S572 | 0.9 | A, spores |
| S571 | 1.2 | B, spores |
| S572 | 1.7 | B, spores |
| S571 | 2.9 | B, mycelium |
| S572 | 3.0 | B, mycelium |
| S571 | 8.4 | C, mycelium |
| S572 | 6.0 | C, mycelium |

We claim:

1. A Phycomyces strain which is an intersexual heterozygote.

2. A Phycomyces strain according to claim 1 which produces β-carotene in an amount of more than 10 mg/g dry weight when grown for 6–8 days on plates containing minimal solid medium.

3. A Phycomyces strain according to claim 1 which is a *Phycomyces blakesleeanus* strain.

4. A method of transforming Phycomyces comprising the following steps;

isolating the DNA of a Phycomyces strain having either a (+) or a (−) mating type;

preparing a gene bank by cloning said DNA in a vector; and introducing said vector via microinjection into a Phycomyces strain of the opposite mating type.

5. A method for obtaining an intersexual heterozygous Phycomyces comprising the steps of:

isolating the DNA of a Phycomyces swain having either a (+) or a (−) mating type;

preparing a gene bank by clotting said DNA in a vector;

introducing said vector via microinjection into a Phycomyces strain of the opposite mating type; and screening for intersexual heterozygous strains.

6. A process for producing β-carotene from an organism according to claim 1, comprising the steps of:

cultivating an intersexual heterozygous organism from a Phycomyces strain in a culture medium produce mycelia;

harvesting said mycelia; and extracting β-carotene from said mycelia.

7. A process according to claim 6 Wherein the intersexual heterozygous Phycomyces is grown in a submerged culture.

* * * * *